(12) United States Patent
van Haeringen et al.

(10) Patent No.: US 6,686,160 B2
(45) Date of Patent: Feb. 3, 2004

(54) UNIVERSAL VARIABLE FRAGMENTS

(75) Inventors: Willem Anne van Haeringen, Veenendaal (NL); Hendrik van Haeringen, Veenendaal (NL)

(73) Assignee: Dr. Van Haeringen Laboratorium B.V., Wageningen (NL)

( * ) Notice: Subject to any disclaimer, the term of this patent is extended or adjusted under 35 U.S.C. 154(b) by 0 days.

(21) Appl. No.: 09/958,221

(22) PCT Filed: Mar. 5, 2001

(86) PCT No.: PCT/NL01/00177

§ 371 (c)(1),
(2), (4) Date: Apr. 15, 2002

(87) PCT Pub. No.: WO01/64948

PCT Pub. Date: Sep. 7, 2001

(65) Prior Publication Data

US 2003/0017471 A1 Jan. 23, 2003

(30) Foreign Application Priority Data

Mar. 3, 2000 (EP) .............................................. 00200757

(51) Int. Cl.$^7$ ........................... C12Q 1/68; C12P 19/34; C07H 21/04

(52) U.S. Cl. ......................... 435/6; 435/91.1; 435/91.2; 536/24.3; 536/24.32; 536/24.33; 536/23.1

(58) Field of Search .......................... 435/6, 91.1, 91.2; 536/23.1, 24.3, 24.32, 24.33

(56) References Cited

U.S. PATENT DOCUMENTS 5,691,136 A * 11/1997 Lupski et al. .................. 435/6
5,955,276 A * 9/1999 Morgante et al. ............... 435/6

FOREIGN PATENT DOCUMENTS

EP 0 721 987 A1 7/1996

OTHER PUBLICATIONS

Caetano–Anolles et al., DNA Amplification Fingerprinting: A Strategy for Genome Analysis. Plant Molecular Biology Reporter, 9(4):294–307, 1991.

Chee et al., Development of Polymerase Chain Reaction for Barley Genome Analysis. Journal of the American Society of Brewing Chemists, 51(3):93–96, 1993.

Davilla et al., Molecular Characterization and genetic mapping of random amplified microsatellite polymorphism in barley. Theoretical and Applied Genetics, 98(2):265–73, 1999.

Pasakinskiene et al., Anchored simple–sequence repeats as primers to generate species–specific DNA markers in Lolium and Festuca grasses. Theoretical and Applied Genetics, 100:384–90, 2000.

Sanchez de la Hoz et al., Simple sequence repeat primers used in polymerase chain reaction amplifications to study genetic diversity in barley. Genome, 39(1):112–17, 1996.

Vos et al., AFLP:a new technique for DNA fingerprinting. Nucleic Acids Research, 23(21):4407–14, 1995.

Wu et al., Detection of microsatellite polymorphisms without cloning. Nuleic Acids Research, 22(15):3257–58, 1994.

Zietkiewicz et al., Genome Fingerprinting by Simple Sequence Repeat (SSR)—Anchored Polymerase Chain Reaction Amplification. Genomics, 20:176–83, 1994.

\* cited by examiner

*Primary Examiner*—Kenneth R. Horlick
*Assistant Examiner*—Cynthia Wilder
(74) *Attorney, Agent, or Firm*—TraskBritt

(57) ABSTRACT

Methods and associated kits for analyzing genomic DNA in a sample are provided. The methods comprise providing two oligonucleotide primers, where the first primer comprises a repeat sequence and at least one nucleotide positioned on the primer's 5' end that is inconsistent with the repeat pattern, where the nucleotide localizes the primer to the 5' end of a repeat sequence in the genomic DNA. The second primer is on the 3' side of the repeat sequence in the genomic DNA. The methods also comprise conducting amplification of the DNA sample under conditions such that neither primer alone can amplify DNA, thus producing DNA fragments based on repeat sequences on one end of the genomic DNA and other sequences based on the opposite end of the genomic DNA. The methods further comprise analyzing the amplified products to determine the length of a repeat sequence found in the genomic DNA.

15 Claims, 3 Drawing Sheets

SEQUENCE LISTING

```
<160> NUMBER OF SEQ ID NOS: 27

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: primer

<400> SEQUENCE: 1
cacacacaca ca                                                          12

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: primer

<400> SEQUENCE: 2 cacaca                                                                  6

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: primer

<400> SEQUENCE: 3 ttgtgtgtg                                                               9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: primer

<400> SEQUENCE: 4 atgtgtgtg                                                               9

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence: primer

<400> SEQUENCE: 5 ctgtgtgtg                                                               9
```

```
<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: primer

<400> SEQUENCE: 6 ccacacaca                                                                  9

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: primer

<400> SEQUENCE: 7 gcacacaca                                                                  9

<210> SEQ ID NO 8
<211> LENGTH: 9
<212> TYPE: DNA
<213> ORGANISM: Artificial Sequence
<220> FEATURE:
<223> OTHER INFORMATION: Description of Artificial Sequence: primer

<400> SEQUENCE: 8 tcacacaca                                                                  9

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: primer

<400> SEQUENCE: 9
tttgtgtgtg                                                                10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: primer

<400> SEQUENCE: 10
attgtgtgtg                                                                10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (5)..(9)
<223> OTHER INFORMATION: "n" on position 5, 6, 7, 8 and 9 stands for
      inosine

<400> SEQUENCE: 11 atgtnnnnnt                                                                10
```

```
<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (6)..(9)
<223> OTHER INFORMATION: "n" on position 6, 7, 8 and 9 stands for
      inosine

<400> SEQUENCE: 12 atgtcnnnnt                                                          10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (7)..(9)
<223> OTHER INFORMATION: "n" on position 7, 8 and 9 stands for
      inosine

<400> SEQUENCE: 13 atgtctnnnt                                                          10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (2)..(4)
<223> OTHER INFORMATION: "n" on position 2,3 and 4 stands for inosine

<400> SEQUENCE: 14 tnnntgtcag                                                          10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (2)..(4)
<223> OTHER INFORMATION: "n" on position 2, 3 and 4 stands for
      inosine

<400> SEQUENCE: 15 tnnnacgtcg                                                          10

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 16
ttgtgtgtgt gtgtgtg                                                  17
```

```
<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 17
atgtgtgtgt gtgtgtg                                                  17

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 18
ctgtgtgtgt gtgtgtg                                                  17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 19
ccacacacac acacaca                                                  17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 20
gcacacacac acacaca                                                  17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 21
tcacacacac acacaca                                                  17

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (5)..(14)
<223> OTHER INFORMATION: "n" on position 5-9 and 11-14 stands for
      inosine

<400> SEQUENCE: 22
atgtnnnnnt nnnnt                                                    15

<210> SEQ ID NO 23
<211> LENGTH: 16
```

```
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (6)..(14)
<223> OTHER INFORMATION: "n" on position 6-9 and 11-14 stands for
      inosine

<400> SEQUENCE: 23
atgtcnnnnt nnnnta                                                   16

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (2)..(13)
<223> OTHER INFORMATION: "n" on position 2-4 and 11-13 stands for
      inosine

<400> SEQUENCE: 24
tnnntgtcag nnna                                                     14

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (2)..(13)
<223> OTHER INFORMATION: "n" on position 2-4 and 11-13 stands for
      inosine

<400> SEQUENCE: 25
tnnntgtcag nnnaa                                                    15

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (2)..(13)
<223> OTHER INFORMATION: "n" on position 2-4 and 11-13 stands for
      inosine

<400> SEQUENCE: 26
tnnnacgtcg nnna                                                     14

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (2)..(13)
```

-continued

<223> OTHER INFORMATION: "n" on position 2-4 and 11-13 stands for
     inosine

<400> SEQUENCE: 27
tnnnacgtcg nnnaa                                                    15

UNIVERSAL VARIABLE FRAGMENTS

CROSS-REFERENCE TO RELATED APPLICATIONS

This application is a filing under 35 U.S.C. 371 of PCT/NL01/00177, filed Mar. 5, 2001, which claims priority to European Patent Application No. EP00200757.3, filed Mar. 3, 2000.

TECHNICAL FIELD

The invention relates generally to methods and materials for the genetic analysis of an individual organism.

BACKGROUND

For some species, reliable, simple technologies are available for genetic analysis of individuals. However, for most animal and bird species genetic information is insufficient for applied genetics. Developing existing technologies for each species to obtain genetic data will be extremely laborious and time consuming. Progress to date has been slow. The situation is particularly problematic in the area of wildlife management. For example, building DNA-patterns of hawks is currently almost impossible. At the same time, there have been reports of people illegally placing eggs from wild mating hawk couples in tamed breeding hawk nests. It is currently nearly impossible to prove fraud using DNA-data in species where genetic variation has not been previously described.

Other areas of interest are DNA-identification of exotic species (e.g., animals, plants, organisms) for various reasons. For instance, animals arriving through the veterinary control can be identified by sampling them both at departure, as well as at arrival. Using the animal's individual DNA to identify it, animals can be tracked, and proof of their origin always possible.

Furthermore, parentage verification in rare, expensive, animals and strain identification of plants can be performed for any given combination or species. Reports have been made of selling the offspring of 'lower' breeding parents as the highest possible quality animals.

Another problem is the determination of sex. For many exotic species, genetic markers are not available to perform sex determination.

A need exists for a method of quickly genetically analysing a species to determine, among other things, its lineage, sex, and origin.

BRIEF SUMMARY OF THE INVENTION

The invention provides a new technology which has been developed for the quick genetic analysis of a species and individuals thereof. The method includes the use of first and second oligonucleotide primers for performance of a PCR amplification on the genomic DNA. The first oligonucleotide primer is a 5' variation generator, including a repeat sequence and a least one non-repeat nucleotide. The second oligonucleotide primer is a 3' fragment generator starting within such a genetic distance that amplification of the genomic DNA can be performed, and preferably includes inosine. A PCR amplification of the genomic DNA is conducted at a relatively low annealing temperature using both the first and second oligonucleotide primers under conditions such that essentially neither the first nor the second oligonucleotide primer alone can amplify sufficient DNA to be detected. DNA fragments are thus produced based on repeat sequences on one end of the genomic DNA, and other sequences based on the opposite end of the genomic DNA. The resulting PCR products can then be analysed for the length of a repeat sequence found in the genome. A second PCR is preferably conducted on the diluted PCR products of the first PCR. Such a second PCR would be conducted using third and fourth oligonucleotide primers. The third and fourth oligonucleotide primers are elongated versions of the first and second oligonucleotide primers, respectively, thus enabling PCR amplification at relatively higher annealing temperatures, and enabling a selection of a sub-set of the DNA fragments amplified in the first PCR. At any point, an optional but preferred restriction digestion may be conducted. The technology has been developed for the quick genetic analysis of a species which is reliable, reproducible, simple, and useful for all species/organisms (e.g., animal, avian, bacterial, viral, and plant). The invention particularly relates to samples obtainable from non-human species but is applicable to samples obtained from humans as well. Neither variation in genome length nor genome composition appears to influence or limit the characteristics of the technology. The new technology is generally reliable, reproducible, simple, and useful for all species/organisms (e.g., animal, avian, bacterial, viral, and plant). Furthermore, any material containing DNA (e.g., blood, hair follicles, etc.) can be used as a source for the generation of DNA-patterns.

In one aspect, the invention includes a method of analysing genomic DNA in a sample. This method includes providing first and second oligonucleotide primers, wherein the first oligonucleotide primer is a "5' variation generator" comprising a repeat sequence and at least one non-repeat nucleotide on the first oligonucleotide's 5' end. Meanwhile, the second oligonucleotide primer is a "3' fragment generator" starting within such a genetic distance that amplification of the genomic DNA can be performed. A nucleic acid amplification such as a polymerase chain reaction ("PCR") amplification is conducted on the genomic DNA in the sample using both the first and second oligonucleotide primers. The nucleic acid amplification is conducted under conditions such that neither the first nor the second oligonucleotide primer alone amplifies DNA, thus producing DNA fragments based on repeat sequences on one end of the genomic DNA and other sequences based on the opposite end of the genomic DNA. The amplified products are then analysed to determine the length of a repeat sequence found in said genomic DNA, which can be compared with the DNA putatively of the same individual or the DNA of the individual's putative ancestors or relatives.

Alternatively, and as more thoroughly described hereinafter, multiple amplifications and/or restriction digestion might also be used with the technique.

As described, the first primer, the "5' variation generator", includes a complementary repeat sequence and at least one non-repeat nucleotide so as to start the amplification at a repeat sequence of the genomic DNA.

By localising the 5' variation generator at the 5' site of repeat sequences, the repeat length variation is enclosed in the amplification rounds. Primers are thus bound to hybridise at the 5' ends of repeat sequences by addition of one or more nucleotides at the end of the primer.

While the oligonucleotide primers at repeat sequences provide detection of genetic variation, the 3' fragment generator is used to amplify fragments of reasonable sizes (e.g., 100 base pairs to 10 kb). The 3' fragment generator starts within such a genetic distance, that amplification of a sample DNA can be perform, and preferably includes inosine or another a-selective base allowing to influence annealing temperatures without coincident or equal influence on the stringency of the annealing reaction. The 3' fragment generator is designed to anneal to the DNA within a short distance—as mentioned before. To do this, the number of selective nucleotides is kept at a low number, whereas the annealing temperature is influenced by a number of non-selective nucleotides, such as inosines, universal bases, and any combination of A,C,G or T (e.g. R,Y,N. By providing the use of such a 3' fragment generator the invention provides optimal reaction conditions in the reaction, generally well suited to the reaction conditions required for the 5' generator. In short, the number of selective nucleotides of this primer is maintained at a relatively low number, whereby the annealing temperature is raised to enable reliable and reproducible amplification, using a-selective bases such as inosines in the fragment generator oligonucleotide.

Some of the genetic markers identified using the technology will be located on the male and female sex-chromosomes. After the identification of such markers, these markers can be used to determine the sex of species, which are difficult to establish through phenotypic characteristics (e.g., porcupine or crocodile).

The invention also includes a kit of parts for performing the genetic analysis, and a method of manufacturing such kit for use in genetic analysis. The invention is further described in the detailed description without limiting the invention thereto

BRIEF DESCRIPTION OF THE DRAWINGS

The samples used in the illustrations are based on high molecular weight DNA obtained from blood samples from each animal.

DETAILED DESCRIPTION OF THE INVENTION

Figure 1:
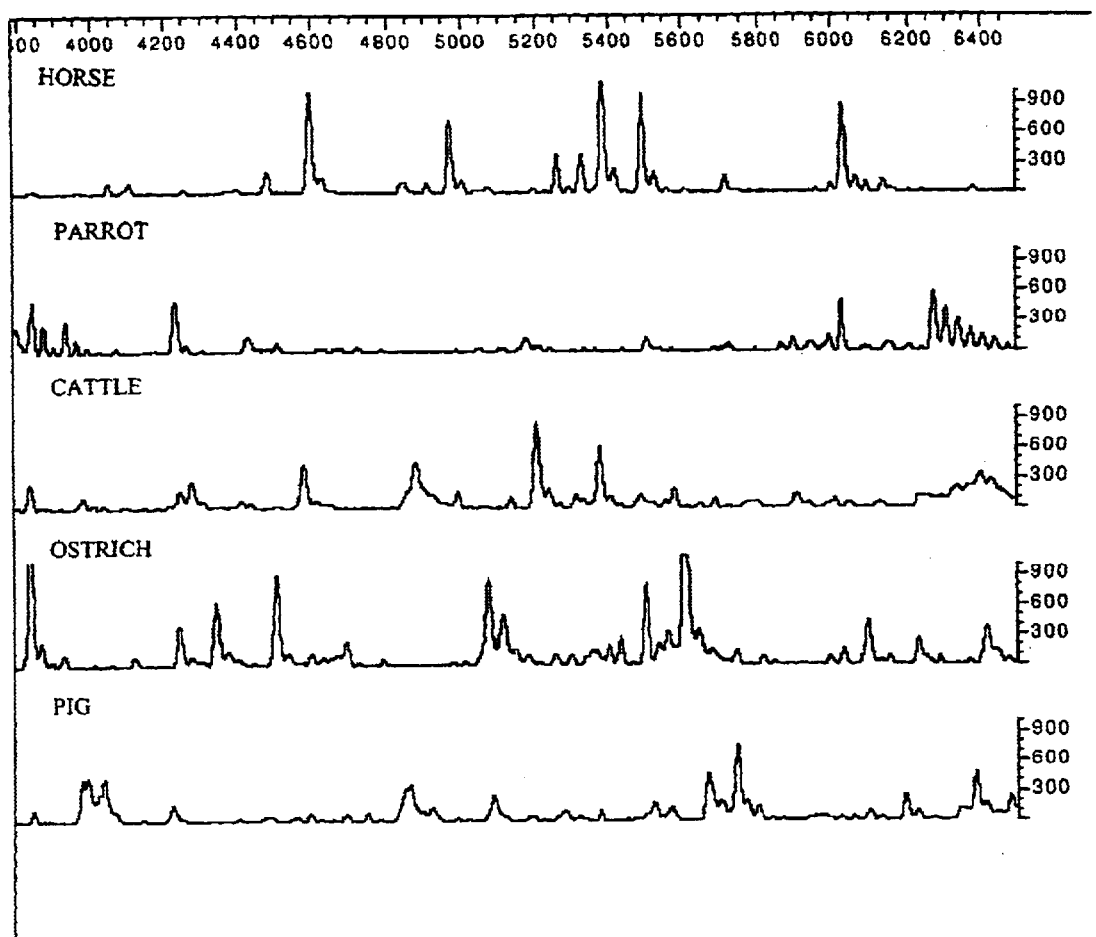
FIG. 1 illustrates the analyses of five species. Clear differences are present. Different lanes present 1) horse, 2) parrot, 3) cattle, 4) ostrich and 5) pig. The illustration shows DNA fragments ranging form sizes between 100 and 1200 bp.
Figure 2:
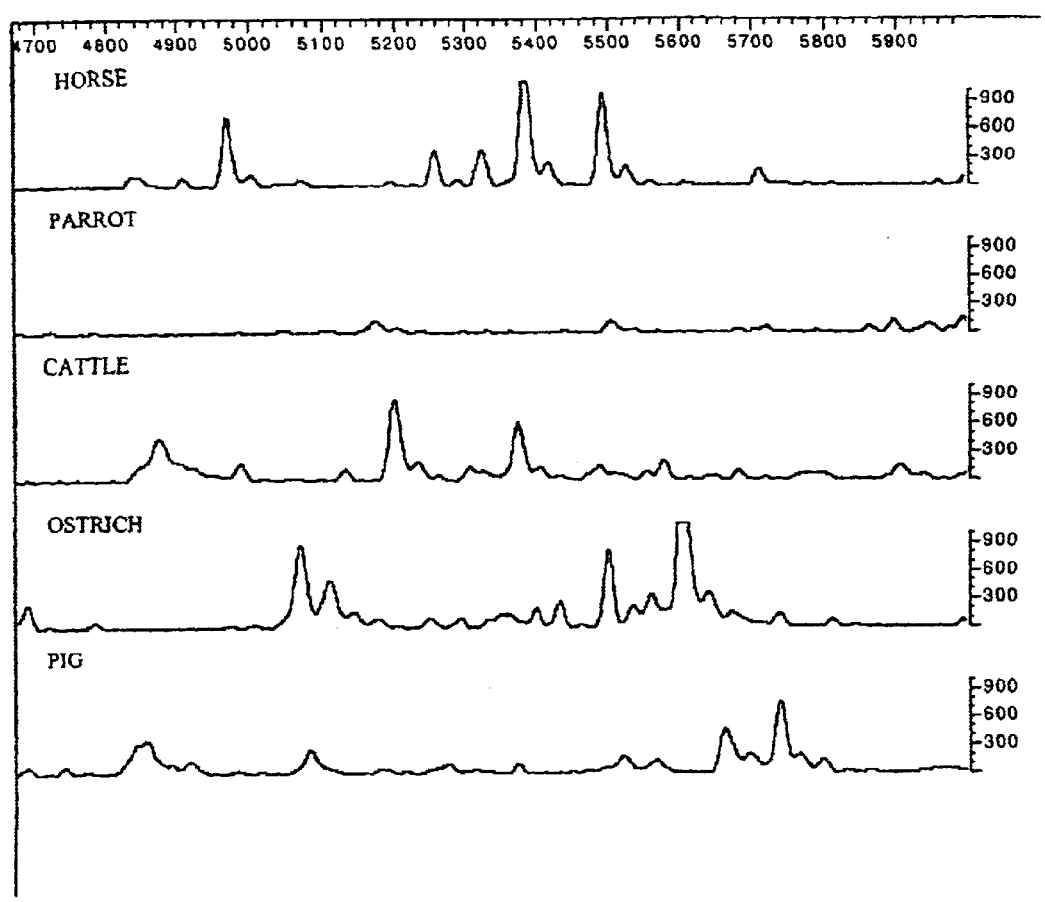
FIG. 2 is an illustration of the analyses of five species. Clear differences are present. Different lanes are present 1) horse, 2) parrot, 3) cattle, 4) ostrich and 5) pig. The illustration shows DNA fragments ranging from sizes between 250 and 300 bp.
Figure 3:
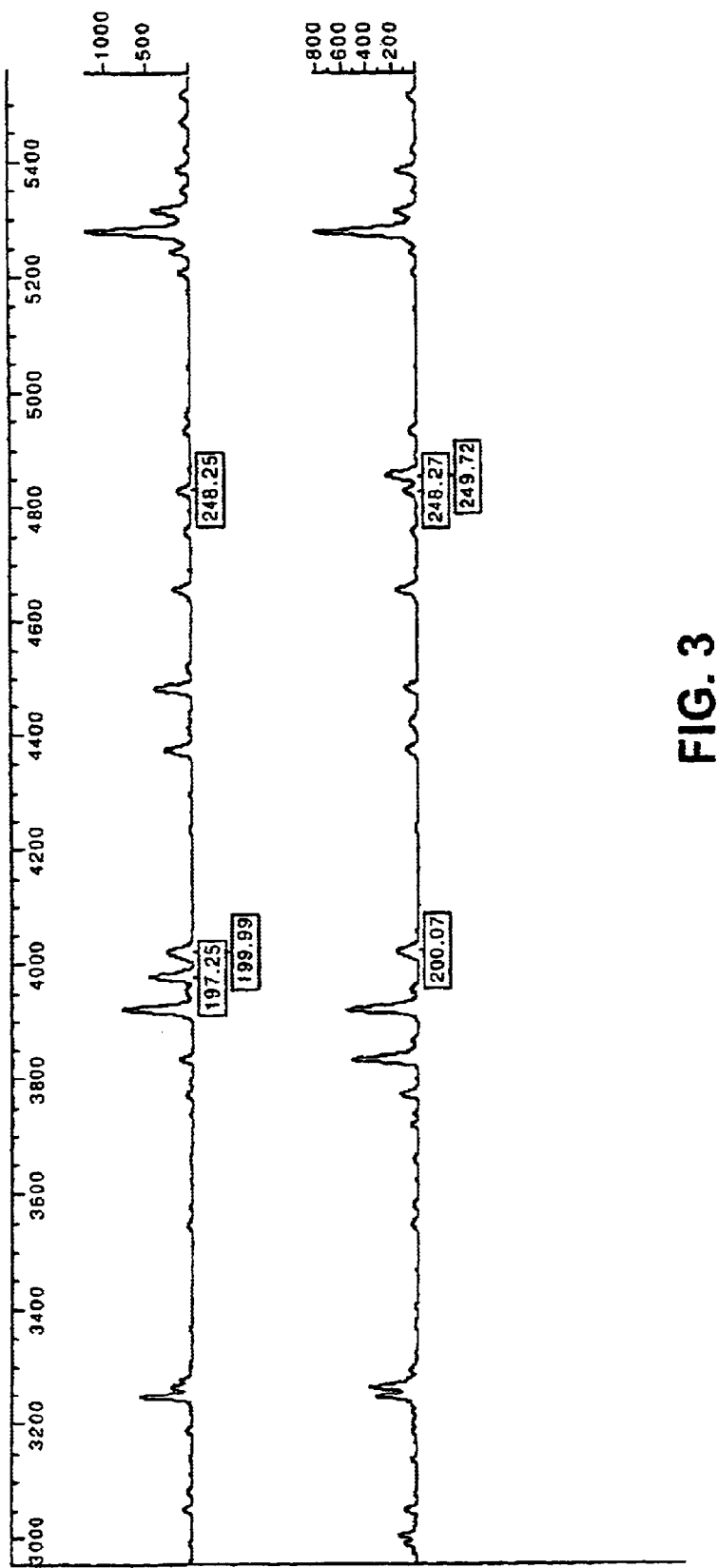
FIG. 3 depicts the variation within species. Two samples of the same species (ostrich) are presented. At least three loci are presented.

To combine the amplification of many DNA-fragments with the selection of a specific set of informative DNA-fragments, a preferred protocol is used which is based on two subsequent PCR amplifications. PCR is one of many well known amplification methods known in the art, and will not be described further here.

In a preferred method, genomic DNA from the sample is amplified in a first PCR at relatively low annealing temperatures. The 5' variation generator and the 3' fragment generator are used to generate fragments, of which a selected part is to be used in a second PCR The first PCR is usually run under conditions wherein neither the 5' variation generator nor the 3' fragment generator alone amplify DNA. Thus, when DNA amplification is performed using both the 5' variation generator and the 3' fragment generator, many resulting fragments are based on repeat sequences on one end of the genomic DNA, and, at the same time, many sequences based on an opposite end of an genomic DNA result.

After possible dilution of the PCR products of the first PCR, a second PCR is preferably performed. This second PCR is conducted using third and fourth oligonucleotide primers. The third and fourth oligonucleotide primers are commonly elongated versions of the first and second oligonucleotide primers, respectively, thus enabling PCR amplification at relatively higher annealing temperatures, and enabling a selection of a sub-set of the DNA fragments amplified in the first PCR. The fourth oligonucleotide primer preferably includes inosine residues.

At any point during this procedure, a preferred, but optional, restriction digestion may take place. Another source of genetic variation in amplified fragments is the presence or absence of restriction sites. Addition of a restriction digest after the second PCR increases the number of genetic polymorphisms detected. Furthermore, the sizes of the DNA fragments to be analysed for their length are decreased as well.

The amplified PCR products can then be analysed using a variety of existing methods.

As can be determined, in the first PCR amplification, many DNA-fragments are amplified, whereas in the second PCR amplification, a subset of these DNA-fragments are multiplied. Both reactions are preferably run under stringent conditions. Primers used in the PCR procedure can vary in length. Lengths between 4 and 50 nucleotides or inosines were used in the examples.

Primer Design

As previously identified, the variation generator starts at a repeat sequence, while the fragment generator starts within such a genetic distance, that amplification of the DNA can be performed.

For the 5' variation generator, repeat sequences exist throughout any genome in many variations, such as mononucleotide (A, G, C or T) repeat, dinucleotide (CT, CA, CG, AT, AC, AG, GT, GC, GA, TA, TG and TC) repeat, trinucleotide (e.g., TGA, CTG, etc.) repeat, tetranucleotide (e.g., TGCA, CTGT) repeat, and so forth. For instance, an AC repeat can have the structure: CACACACACACA (SEQ ID NO:1) ("6-repeat"), or CACACA (SEQ ID NO:2) (3-repeat).

Repeat sequences of course also exist in the as yet unanalysed genomes of species. Repeat sequences exhibit different lengths due to the number of repeats present. For different individuals, differences exist in the numbers of repeats in each locus ("microsatellite"). Thus, genetic variation in repeat sequences can he determined based upon length variation caused by the number of nucleotide repeats in a locus. The number of repeats in a microsatellite can vary enormously with different individuals of the species. Many sequences contain a few repeats (e.g., 2 or 3), whereas some repeats are known to include thousands of base pairs ("bp").

By localising the oligonucleotide primer at the 5' site of repeat sequences as described herein, the repeat length variation is enclosed in the amplification rounds which are part of PCR. Primers are forced to hybridise at 5' ends of repeat sequences by adding one or more nucleotides which do not continue the repeat pattern at the 5' end of the primer. This result is due to the nature of the amplifying enzyme, which elongates DNA-fragments starting from the 3'-end of oligonucleotide primers.

While the choice of oligonucleotide primers at repeat sequences provides most the detection of genetic variation, the 3' fragment generator is essentially used to amplify fragments of reasonable sizes (100 bp to 10 kb).

The number of selective oligonucleotides of the primer is maintained at a low number. The annealing temperature at the same time, is raised to enable reliable and reproducible amplification. This is done using inosine substitutions in the fragment generator. Inosines are used to increase annealing temperatures without affecting the binding conditions of oligonucleotides. Inosines match to any of the four nucleotides in the DNA. When inosine is substituted for a nucleic acid, it contributes to the sensitivity of the technique.

PCR

To combine the amplification of many DNA-fragments with the selection of a specific set of informative DNA-fragments, a protocol is used which is based on two subsequent PCR-amplifications. In the first PCR amplification, many DNA-fragments are amplified, whereas in the second PCR amplification, a subset of these DNA-fragments are multiplied. Both reactions are run under stringent conditions.

After the PCR (or PCRs) have been conducted, the resulting amplified fragments are preferably subjected to restriction digestion to determine the presence or absence of restriction sites. Use of the restriction enzymes increases the number of genetic polymorphisms detected.

The preferably digested) product is then sequenced using techniques known in the art to determine the particular genetic patterns or markers present, when so desired.

Applications

The nature of universal variable fragments (UVF) combines flexibility and reproducibility with high levels of polymorphisms. The Variation Generator (based on the microsatellite sequence) mostly corresponds with genetic variation typically found in microsatellites, whereas the Fragment Generator is mainly linked to presence/absence polymorphisms. This strategy is typically based on the use of two different fluorescent labels—one associated with the Variation Generator, the other corresponding to the Fragment Generator. This concept enables the optimal use of high throughput analysis systems based on multiple fluorescent dyes.

In comparison with other technologies, e.g. AFLP, UVF has an increased power to generate polymorphisms in search for high marker density. One distinct advantage of the UVF system is found in the possibility to increase the marker density in regions of chromosomes of specific interest by choosing the order of the bases of the Fragment Generator—instead of random in the flanking region of a known genetic marker. As a result, a number of genetic markers can be identified within a short distance from e.g. QTL-markers. This prospect is not possible with other technologies such as AFLP (and SAMPL), or ISSR (Inter Simple Sequence Repeat).

Compared to Several Technologies UVF is Different a) The power to generate polymorphisms is much larger compared to RAPD (random amplified polymorphism detection). Due to it's concept of a three step strategy, UVF has increased power to generate polymorphisms. RAPD is based on only one primer in just one PCR, whereas UVF is typically based on two consequent PCR amplifications, followed by a digestion step.

b) Amplification using ISSR (Inter Simple Sequence Repeat) is based on one primer in one PCR reaction. UVF is completely different based on typically two PCR amplifications and the use of a digestion step.

c) Amplified Fragment Length Polymorphisms (AFLP) is based on the use of adaptor ligation to initiate PCR. This procedure is topically completely absent in UVF, as is the obligation to start the reaction with a digestion of several restriction enzymes.

d) SAMPL is completely based on AFLP, but is directed to the detection of microsatellites using the AFLP technology.

Furthermore, compared to RAPD and microsatellite analysis the power to generate large amounts of polymorphisms from a small amount of genomic DNA is clear.

Several Areas For Applications Based on UVF Include

1. Gene hunting

The detection and identification of genetic markers for diseases or beneficial genetic characteristics is possible using UVF. Due to its effectiveness, even in species with a relatively well-developed genetic map UVF is useful. In other species where the number of available genetic markers is low, UVF will be the technology of choice.

2. Marker density

In situations where QTL-analysis has revealed a genetic marker (e.g. RFLP or microsatellite) with known sequence the number of markers in a defined region can be increased using the UVF technology. This can be achieved by locating the nine bases of the Fragment Generator in the flanking region of the polymorphic marker. This enables generation of genetic markers in specific areas of interest. Using this approach, the range in which QTLs may be located can be decreased, and e.g. 'candidate gene approach' can be more directed.

This strategy can be further used to detect genetic variation in the genomic regions close to promoter sites located close to genes. The design of the Fragment Generator can be based on general promoter sites, or based on sequences recognized by transcription factors. This further illustrates the power of UVF over other available technologies.

3. Forensic Analysis

Due to the nature of UVF, small quantities of DNA can be used to generate DNA-profiles. This enables the use of UVF in situations where only limited amounts of DNA are available for genetic analysis—e.g. forensics.

4. Biodiversity

UVF enables the search for breed- and species-specific markers. Amongst other issues, (sub)-species identification of for example birds will solve many enduring discussions.

In use, the invention is quite straightforward. The invention provides rapid and straightforward identification of endangered animals and plants. Many wildlife species—both animals and plants—are protected by law. Only limited numbers of individuals may be kept in private. However, identification and lineage of these individuals needs to be proven to effectively protect the law. The invention provides the means to answer any question in wildlife management relating to identity or lineage, also of species of which specific sequences are little known. The invention also provides genetic maps of a species. In some species genetic information, and certainly genetic maps are underdeveloped. Usually, identification of genetic markers is time and labour consuming using the existing methodologies (e.g. microsatellites).

Furthermore, testing of these markers is inefficient due to the low number of genetic markers amplified in one, single, reaction.

With the new technology genetic markers are developed at low costs with high speed and efficiency. Thus, 'classical' laborious methods are no longer needed, and no individual primer sets for each marker is needed. Furthermore, using the invention, many genetic markers can be identified, and analysed in a short period of time. Further analysis of the segregation of these markers in families where diseases, resistance genes, or other genes of interest are segregating as well will enable the identification of genetic markers related to the genes of interest.

In the case where lineage is in question, once the genetic markers of the individual have been determined, they can likewise be determined for the putative parents. The sets of markers (e.g., the number of repeats in a locus the length variation of the set of amplified fragments, and so on) from an individual can then be compared with the markers of the putative parent or parents, and a determination of lineage made. In the case of the aforementioned hawk, for instance, if the number of repeats in a particular locus of the hawk's DNA do not match that of the tamed breeding putative parents, the conclusion can be drawn that the tamed breeding pair are not the parents.

The same situation arises when the question of pedigree arises. The genetic markers of the individual are compared and contrasted with those of the putative ancestors or relatives, especially parents.

In the case of gender determination, a library would first be constructed of the particular species (e.g., crocodile) with particular emphasis put on the Y chromosome. Once conserved genetic markers present on the Y chromosome are identified for the species, the DNA of the individual in question can be analysed with the instant invention.

When the question centers around whether or not an individual of a species is the same individual previously tested (e.g., by a nation's health, agricultural, or racing authorities), the individual is tested at a different time, and the results are compared with those of the earlier analysis.

A kit of parts for use with the invention includes first and second oligonucleotide primers for performance of the first polymerase chain reaction amplification on the genomic DNA of the individual. The first oligonucleotide primer is a 5' variation generator, starting at a repeat sequence. The second oligonucleotide primer is a 3' fragment generator starting within such a genetic distance that amplification of the genomic DNA can be performed. The kit will also preferably include components for performing the second PCR. Such components include third and fourth oligonucleotide primers, wherein the third oligonucleotide primers is an elongated version of the 5' variation generator, and the fourth oligonucleotide primers is an elongated version of the 3' fragment generator. The kit of parts further also preferably includes appropriate restriction enzymes.

The invention is further explained by use of the following illustrative examples. In the examples, only a limited number of primers are shown. However, any combination of primers based on the information presented herein is considered to be using the same principles of this technology.

EXAMPLES

Example I

Primer Design

Using the previously described criteria (e.g., starting at a repeat sequence and localising the variation generator oligonucleotide primer at the 5' site of repeat sequences, and starting within a genetic distance), the hereinafter described examples of feasible primer sequences were determined. As can be seen, the 5' (left) end of the variation generator includes a nucleotide which is not consistent with the existing repeat pattern of the repeat sequence.

PCR 1. Variation generator.

TTGTGTGTG (SEQ ID NO:3)
ATGTGTGTG (SEQ ID NO:4)
CTGTGTGTG (SEQ ID NO:5)
CCACACACA (SEQ ID NO:6)
GCACACACA (SEQ ID NO:7)
TCACACACA (SEQ ID NO:8)
TTTGTGTGTG (SEQ ID NO:9)
ATTGTGTGTG (SEQ ID NO:10)

Fragment generator.

ATGTIIIIT (SEQ ID NO:11)
ATGTCIIIIT (SEQ ID NO:12)
ATGTCTIIIT (SEQ ID NO:13)
TIIITGTCAG (SEQ ID NO:14)
TIIIACGTCG (SEQ ID NO:15)

PCR 1. AMPLIFICATION OF MANY FRAGMENTS

Genomic DNA taken from a sample was amplified in a first PCR at low annealing temperatures (for example 30–65° C., but preferably lower than temperatures used at an optional second round of amplification). The previously described oligonucleotide primers were used to generate fragments. The first PCR was run under conditions, where neither the fragment generator primer nor the variation generator primer alone could amplify DNA.

PCR 2. AMPLIFICATION OF A SUB-SET OF PCR 1

After dilution of the PCR products of the first PCR, a second PCR was conducted using the resulting fragments. This second PCR was based on the hereinafter described fragment and variation generators, which, as can be seen, were elongated to enable PCR amplification at higher annealing temperatures (40–70° C.). This enabling the selection of a sub-set of the DNA-fragments amplified in PCR 1.

Examples of the elongated primer sequences

PCR 2. Variation generator.

TTGTGTGTGTGTGTG (SEQ ID NO:16)
ATGTGTGTGTGTGTG (SEQ ID NO:17)
CTGTGTGTGTGTGTG (SEQ ID NO:18)
CCACACACACACACA (SEQ ID NO:19)
GCACACACACACACA (SEQ ID NO:20)
TCACACACACACACA (SEQ ID NO:21)

Fragment generator. Six examples are shown:

ATGTIIIIITIIIIT (SEQ ID NO:22)
ATGTCIIIITIIIITA (SEQ ID NO:23)
TIIITGTCAGIIIA (SEQ ID NO:24)
TIIITGTCAGIIIAA (SEQ ID NO:25)
TIIIACGTCGIIIA (SEQ ID NO:26)
TIIIACGTCGIIIAA (SEQ ID NO:27)

The thus amplified PCR products were digested with restriction enzymes such as BamHI or HinfI increasing the number of genetic polymorphisms detected and reducing the sizes of the DNA fragments to be analysed.

ANALYSIS

Analysis of the digested product was conducted on a ABI 377 sequencer (Perkin Elmer, Calif., USA). The detection on this sequencer was made possible through the use of fluorescently labelled primers (both the 5' variation generator and the 3' fragment generator were labelled with different dyes (such as FAM, HEX).

Analysis of the various fragment sizes was performed using the software GENESCAN™ and GENOTYPER™ (both from Perkin Elmer, Calif., USA).

What is claimed is:

1. A method of analysing genomic DNA comprising a repeat sequence in a sample, said method comprising:

provinding first and second oligonucleotide primers, said first oligonucleotide primer comprising a repeat sequence and at least one nucleotide inconsistent with the repeat pattern positioned on the first oligonucleotide primer's 5' end, where said nucleotide localizes the first oligonucleotide primer to the 5' end of a repeat sequence in the genomic DNA sample, and said second oligonucleotide primer starting within such a genetic distance on the 3' side of the repeat sequence in the genomic DNA sample that amplification of the genomic DNA can be performed;

conducting a nucleic acid amplification on said genomic DNA in the sample using both the first and second oligonucleotide primers, thus producing DNA fragments based on repeat sequences on at least one end of the genomic DNA; and analyzing an amplified product thus produced to determine its length.

2. The method according to claim 1 further comprising, conducing a second amplification on the products of the nucleic acid amplification, said second amplification being conducted using third and fourth oligonucleotide primers, said third and fourth oligonucleotide primers being elongated versions of said first and second oligonucleotide primers, respectively, enabling a selection of a sub-set of the DNA fragments amplified in the first amplification.

3. The method according to claim 1 further comprising digesting said amplified products with a restriction enzyme thus increasing the number of genetic polymorphisms detected in said genomic DNA and decreasing the sizes of the DNA fragments to be analyzed for their length.

4. The method according to claim 1 wherein the second oligonucleotide primer comprises an a-selective base.

5. The method according to claim 2 wherein the fourth oligonucleotide primer comprises an a-selective base.

6. A method of analyzing genomic DNA comprising a repeat sequence in a sample, said method comprising:

providing first and second oligonucleotide primers for performance of a first polymerase chain reaction amplification on said genomic DNA, said first oligonucleotide primer comprising a repeat sequence and at least one non-repeat nucleotide on the first oligonucleotide primer's 5' end, wherein said non-repeat nucleotide localizes the first oligonucleotide primer to the 5' end of a repeat sequence in the genomic DNA sample, and said second oligonucleotide primer on the 3' side of the repeat sequence in the genomic DNA sample comprising at least one a-selective base;

conducting said first amplification of said genomic DNA at a first temperature permitting both the first and second oligonucleotide primers to anneal to the genomic DNA, thus producing DNA fragments based on repeat sequences on one end of the genomic DNA, and other sequences based on the opposite end of the genomic DNA;

optionally diluting the reaction products of the first amplification;

conducting a second amplification on the reaction products of the first amplification, said second amplification being conducted using third and fourth oligonucleotide primers, said third and fourth oligonucleotide primers being elongated versions of said first and second oligonucleotide primers, respectively, enabling amplification at a second temperature permitting annealing of the primers, where the second annealing temperature is higher than the first annealing temperatures, and enabling a selection of a sub-set of the DNA fragments amplified in the first amplification; and analyzing the sub-set of amplified products.

7. The method according to claim 6 further comprising digesting the amplified products of the first or second amplification with a restriction enzyme thus increasing the number of genetic polymorphisms detected in said genomic DNA and decreasing the sizes of the DNA fragments to be analyzed for their length.

8. The method according to claim 2 further comprising digesting said amplified products with a restriction enzyme thus increasing the number of genetic polymorphisms detected in said genomic DNA and decreasing the sizes of the DNA fragments to be analyzed for their length.

9. The method according to claim 2 wherein the second oligonucleotide primer comprises an a-selective base.

10. The method according to claim 3 wherein the second oligonucleotide primer comprises an a-selective base.

11. The method of claim 4 wherein the a-selective base is inosine.

12. The method of claim 5 wherein the a-selective base is inosine.

13. The method of claim 6 wherein the a-selective base is inosine.

14. The method of claim 9 wherein the a-selective base is inosine.

15. The method of claim 10 wherein the a-selective base is inosine.

* * * * *

UNITED STATES PATENT AND TRADEMARK OFFICE
CERTIFICATE OF CORRECTION

PATENT NO. : 6,686,160 B2
DATED : February 3, 2004
INVENTOR(S) : Willem Anne van Haeringen and Hendrik van Haeringen It is certified that error appears in the above-identified patent and that said Letters Patent is hereby corrected as shown below:

Column 5,
Line 24, change "The preferably digested) product" to -- The (preferably digested) product --

Column 6,
Line 3, change "topically" to -- typically --

Column 8,
Line 25, change "ATGTIIIIIT" to -- ATGTNNNNNT --.
Line 26, change "ATGTCIIIIT" to -- ATGTCNNNNT --
Line 27, change "ATGTCTIIIT" to -- ATGTCTNNNT --
Line 28, change "TIIITGTCAG" to -- TNNNTGTCAG --
Line 29, change "TIIIACGTCG" to -- TNNNACGTCG --

Column 9,
Line 2, change "ATGTIIIIITIIIIT" to -- ATGTNNNNNTNNNNT --
Line 3, change "ATGTCIIIITIIIITA" to -- ATGTCNNNNTNNNNTA --
Line 4, change "TIIITGTCAGIIIA" to -- TNNNTGTCAGNNNA --
Line 5, change "TIIITGTCAGIIIAA" to -- TNNNTGTCAGNNNAA --
Line 6, change "TIIIACGTCGIIIA" to -- TNNNACGTCGNNNA --
Line 7, change "TIIIACGTCGIIIAA" to TNNNACGTCGNNNAA --

Signed and Sealed this

Twentieth Day of July, 2004

JON W. DUDAS
*Acting Director of the United States Patent and Trademark Office*